United States Patent [19]
Chin et al.

[11] Patent Number: 5,267,970
[45] Date of Patent: Dec. 7, 1993

[54] DEVICE FOR ANCHORING TROCAR SLEEVE

[75] Inventors: Albert K. Chin, Palo Alto; Charles Gresl, Jr., San Francisco; Frank T. Watkins, III, Menlo Park, all of Calif.

[73] Assignee: Origin Medsystems, Inc., San Carlos, Calif.

[21] Appl. No.: 786,719

[22] Filed: Nov. 1, 1991

[51] Int. Cl.$^5$ ............................................. A61M 25/02
[52] U.S. Cl. ..................................... 604/175; 604/174
[58] Field of Search ............... 604/174, 177, 178, 179, 604/180; 128/DIG. 26

[56] References Cited

U.S. PATENT DOCUMENTS

| | | | |
|---|---|---|---|
| 3,821,957 | 7/1974 | Riely et al. | 604/178 |
| 3,990,454 | 11/1976 | Schlesinger | 604/180 |
| 4,699,616 | 10/1987 | Nowak et al. | 604/178 |
| 4,735,615 | 4/1988 | Uddo et al. | 604/180 |
| 4,798,592 | 1/1989 | Parks | 604/178 |
| 4,874,380 | 10/1989 | Hesketh | 604/180 |
| 5,026,352 | 6/1991 | Anderson | 604/178 |
| 5,073,169 | 12/1991 | Raiken | 604/180 |

FOREIGN PATENT DOCUMENTS

| | | | |
|---|---|---|---|
| 2517544 | 6/1983 | France | 604/180 |
| 2643269 | 8/1990 | France | 604/180 |
| 1394632 | 5/1975 | United Kingdom | 604/180 |

Primary Examiner—Paul Hirsch
Attorney, Agent, or Firm—Heller, Ehrman, White & McAuliffe

[57] ABSTRACT

A device for mounting a tubular sleeve for an obturator of a trocar to a patient's body includes a sleeve-holding part for attaching to the sleeve and a skin-fixation part for attaching to the patient's skin surface. The sleeve-holding part may be formed by an annular washer made of an elastic material which permits a user to move it longitudinally with respect to the sleeve so as to adjust their relative positions. The skin-fixation part may be a crossbar and a cord attached to the washer at one end and to the crossbar at the other. The cord is stapled to the patient's body for fixation.

2 Claims, 5 Drawing Sheets

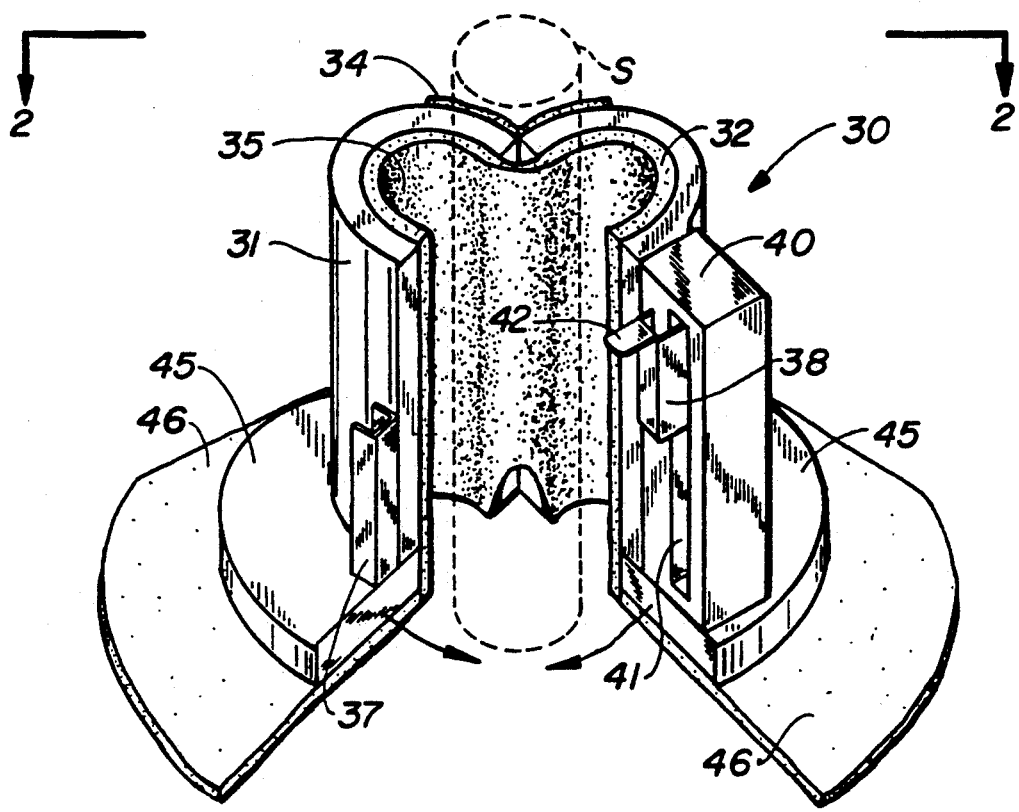
FIG._1
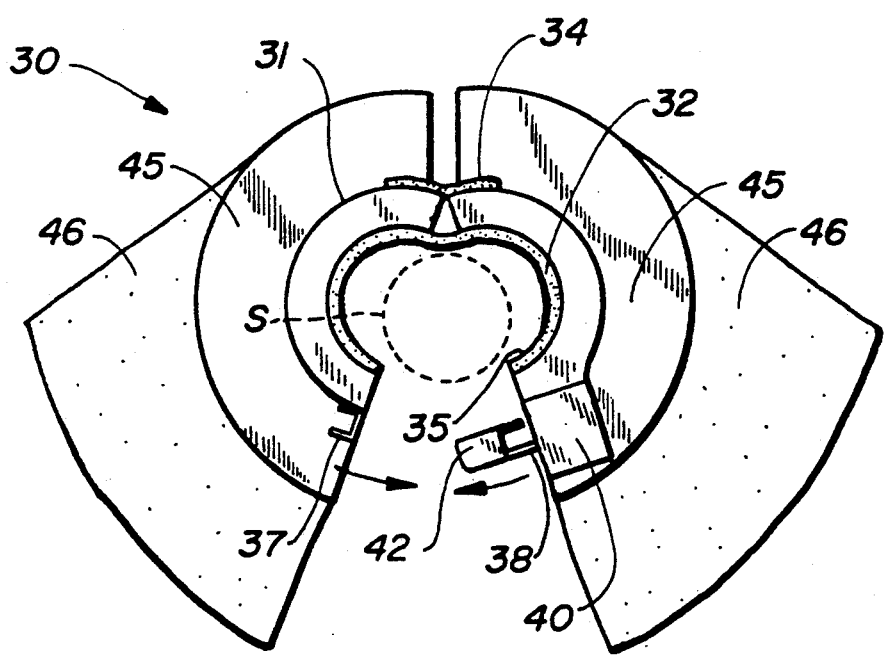
FIG._2

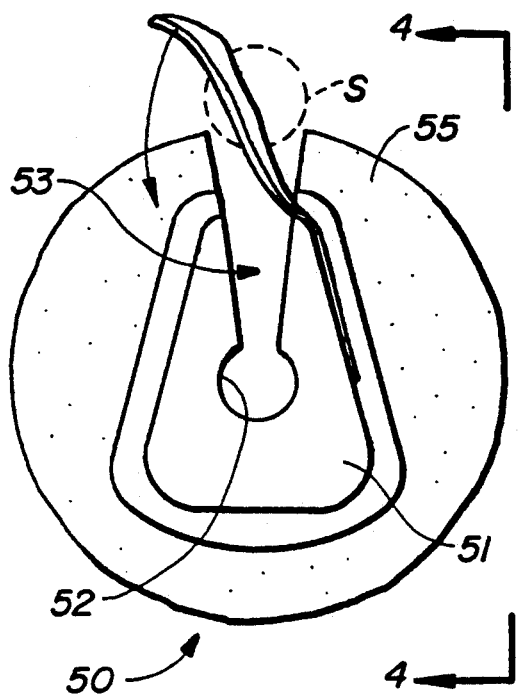
FIG._3
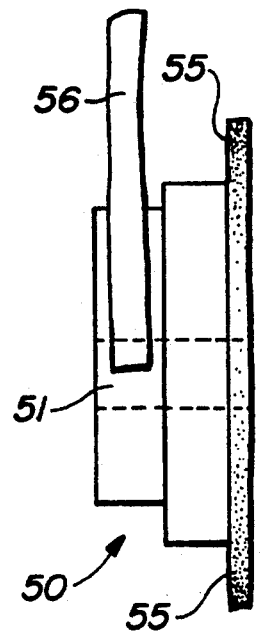
FIG._4
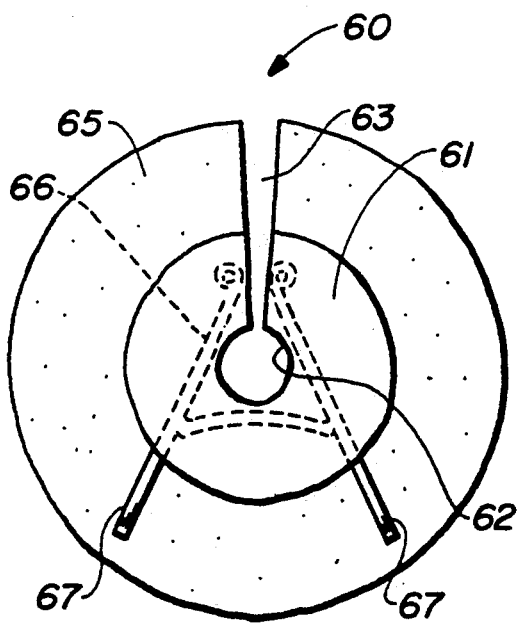
FIG._5
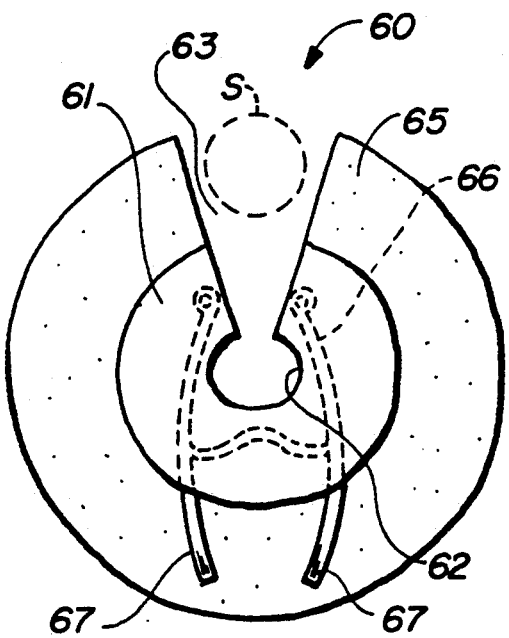
FIG._6

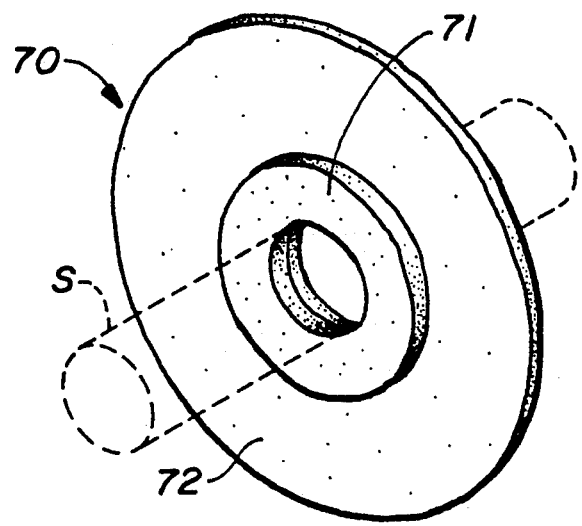
FIG._7
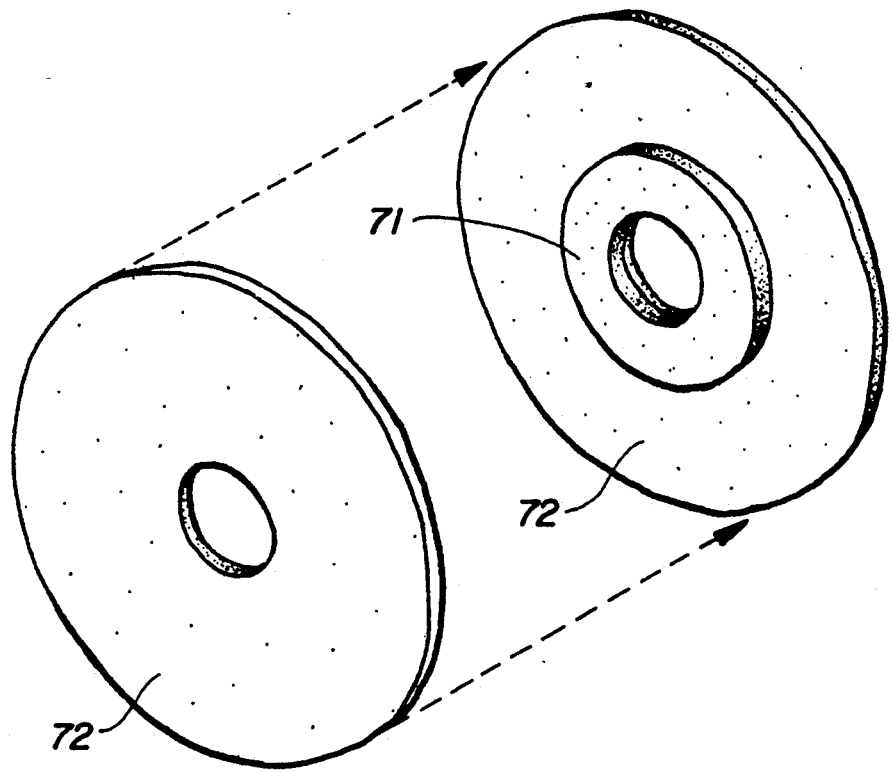
FIG._8

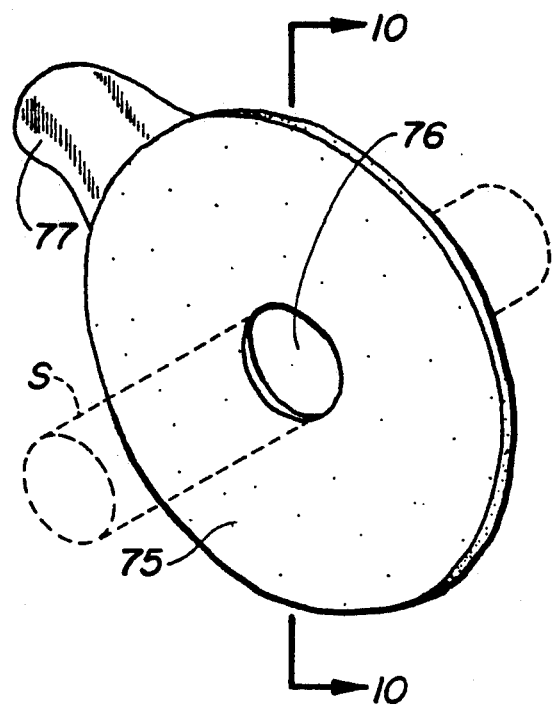
FIG._9
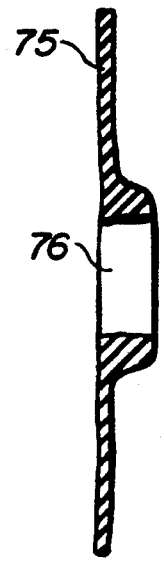
FIG._10
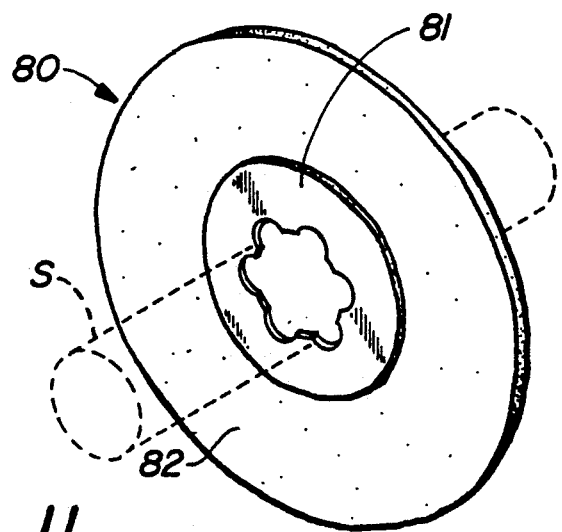
FIG._11

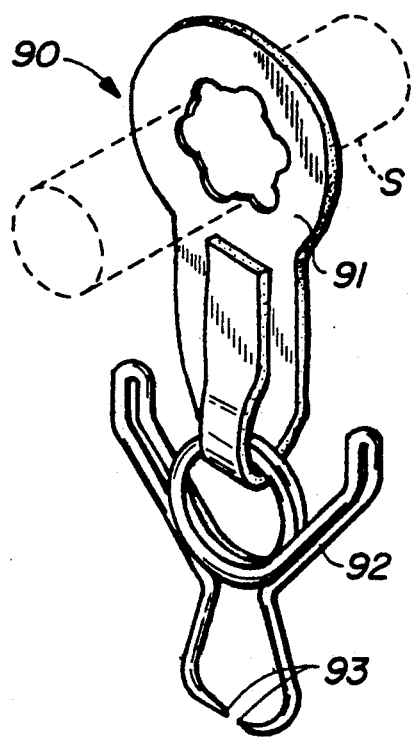
FIG._12
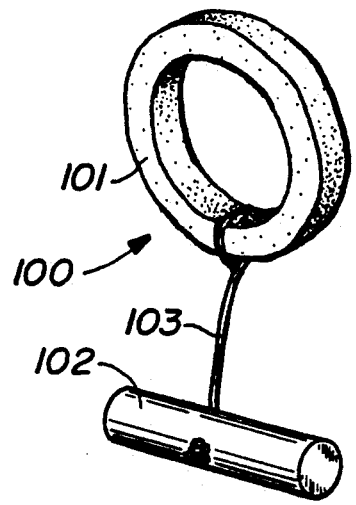
FIG._14
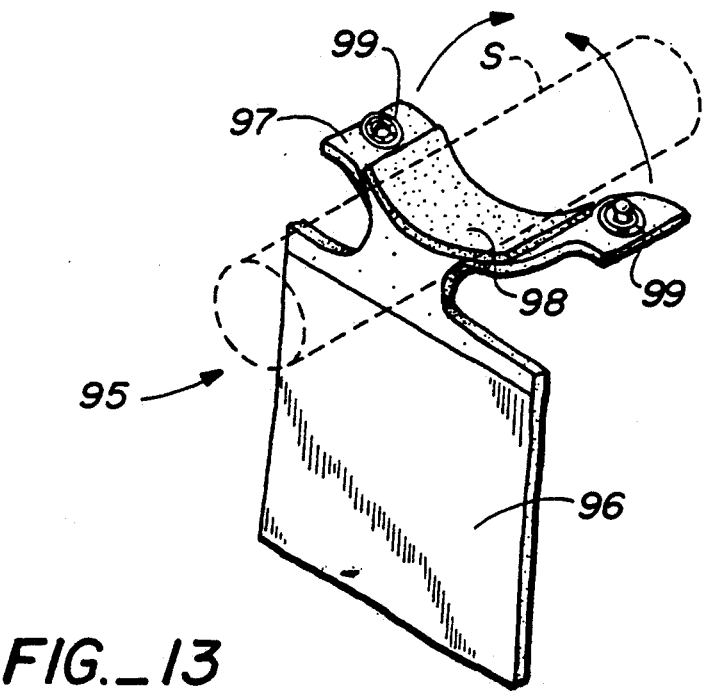
FIG._13

DEVICE FOR ANCHORING TROCAR SLEEVE

BACKGROUND OF THE INVENTION

This invention relates to devices for anchoring a trocar sleeve to a patient's body. More particularly, this invention relates to such devices by which the longitudinal position of the sleeve with respect to the patient's body can be easily adjusted.

Trocars are surgical instruments having an obturator with a sharp pointed stylet for piercing a body wall and a tubular sleeve which surrounds the obturator. A trocar assembly thus formed is manually forced by a surgeon with the sharp stylet of the obturator serving to pierce the body wall so as to provide an opening for the tubular sleeve. After the trocar sleeve is in communication with a body cavity, the obturator is removed such that an endoscopic instrument may be inserted into the cavity through the sleeve for performing endoscopic surgery within the cavity.

The trocar sleeve, in order to thus serve as a passageway for various surgical instruments, must remain securely anchored to the patient's body so as not to be easily pulled out of its inserted position. A currently available prior art device for serving this purpose may be characterized as being of a double-gasket structure with an inner tubular member mounted to the sleeve and an outer tubular plug engaging with the inner tubular member and having a helical thread on its outer surface. With a prior art device thus structured, the longitudinal position of the sleeve is not easily adjustable with respect to the patient's body.

SUMMARY OF THE INVENTION

It is a general object of the present invention to provide an improved device for anchoring a trocar sleeve to a patient's body.

It is a specific object of the invention to provide a device for adjustably anchoring a trocar sleeve to a patient's body such that the longitudinal position of the sleeve can be easily adjusted with respect to the patient's body.

It is another object of the invention to provide such a device that is simple in structure and inexpensive to produce.

Devices embodying the present invention, with which the above and other objects can be accomplished, may be broadly characterized as being a simple structure with a sleeve-holding part and a skin-fixation part. The skin-fixation part is for attaching to a patient's skin surface. The sleeve-holding part is basically for securely attaching to a cylindrical object such as a trocar sleeve, but in such a manner that a user can still move it longitudinally with respect to such an object to which it has been attached. In one of its simplest forms, the sleeve-holding part may be an annular rubber washer because a rubber washer with a proper inner diameter can be tightly wrapped around a cylindrical object but can still be made to slide longitudinally on such an object. Alternatively, use may be made of a generally U-shaped resilient member to envelop the sleeve. An adhesive tape may be used to keep the resilient member in a condition of intimately hugging the sleeve such that the sleeve cannot easily slide off, or the biasing force of a metal spring may be used for the same purpose. The skin-fixation part may be in the form of a pad having an adhesive surface, a pad which can be fastened to a skin surface by skin staples, or a spring-biased clip which either penetrates or pinches the patient's skin surface.

A device thus formed may be attached to the sleeve before the trocar pierces the patients' body wall but its position relative to the sleeve is easily adjustable. After the sleeve is inserted through the patients' body and reaches a body cavity of interest, the position of the sleeve-holding part is adjusted for the convenience of the attachment of the skin-fixation part onto the patient's skin.

BRIEF DESCRIPTION OF THE DRAWINGS

The accompanying drawings, which are incorporated in and form a part of this specification, illustrate embodiments of the invention and, together with the description, serve to explain the principles of the invention. In the drawings:

FIG. 1 is a perspective view of a mechanical sleeve lock embodying the present invention;

FIG. 2 is a plan view of the mechanical sleeve lock of FIG. 1 taken from the line 2—2 therein;

FIG. 3 is a plan view of another sleeve lock embodying the present invention;

FIG. 4 is a side view of the sleeve lock of FIG. 3 taken from the line 4—4 therein;

FIG. 5 is a plan view of a spring clip sleeve lock embodying the present invention when there is no external force applied thereto;

FIG. 6 is another plan view of the spring clip sleeve lock of FIG. 5 when an external force is applied on its spring clip in preparation for its attachment onto a trocar sleeve;

FIG. 7 is a perspective view of a washer sleeve lock embodying the present invention;

FIG. 8 is a perspective exploded view of another washer sleeve lock embodying the present invention;

FIG. 9 is a perspective view of still another washer sleeve lock embodying the present invention;

FIG. 10 is a sectional view of the washer sleeve of FIG. 9 taken along the line 10—10 in FIG. 9;

FIG. 11 is a perspective view of still another washer sleeve lock embodying the present invention;

FIG. 12 is a perspective view of a clipping type washer sleeve lock embodying the present invention;

FIG. 13 is a perspective view of a snap-on type of sleeve lock embodying the present invention; and FIG. 14 is a perspective view of a stapling type of washer sleeve lock embodying the present invention.

DETAILED DESCRIPTION OF THE INVENTION

As shown in FIGS. 1 and 2, a mechanical sleeve lock 30 embodying the present invention may be characterized as having a pair of curved sleeve-holding wall members 31 and 32 which are hinged together so as to be able to open and close with respect to each other and to together form a hollow cylindrical tube when they are in the closed position. In other words, these curved wall members 31 and 32 each have a semicircular cross-section, having a concave inner surface and a convex outer surface. To serve as the "hinge," a flexible adhesive tape 34 is attached to the outer surfaces of both of the wall members 31 and 32. An adhesive lining 35, made of a flexible material such as elastomer and having a friction-providing surface, is attached to the both inner surfaces of the wall members 31 and 32. The curvature of these inner surfaces is such that, when the wall members 31 and 32 are closed as indicated by the arrows in FIGS. 1 and 2, the friction-providing surface of the lining 35 on their inner surfaces will securely hug a trocar sleeve (shown by broken lines and indicated by letter S) and prevent it from sliding longitudinally with respect to the sleeve lock 30 Alternatively, the hinge may be formed of a thin bridge (not shown) of plastic molded integrally to the wall members 31 and 32, and the friction-providing surface may be formed of splines molded in the inner walls of the members 31 and 32.

In order to keep the two sleeve-holding wall members 31 and 32 in the closed condition, there is provided a simple locking mechanism including an elongated, cross-sectionally U-shaped piece 37 attached to one of the wall members (31) along its free edge (away from its hinged edge) and a hooking piece 38 which is so shaped as to be engageable with the cross-sectionally U-shaped piece 37. An elongated structure 40 with a longitudinally extending groove 41 is attached to the other of the wall members (32) along its free edge (away from its hinged edge). The hooking piece 38 is mounted to this elongated structure 40 so as to be slidable along its groove 41. The hooking piece 38 is provided with a unistructurally formed tongue-like protruding part 42, by which a user can easily push the hooking piece 38 along the groove 41 towards the cross-sectionally U-shaped piece 37 to engage them together, thereby keeping the two wall members 31 and 32 in closed condition.

Each of the wall members 31 and 32 is provided with a nearly semicircular flange 45, to which is attached a flexible pad 46 having its back surface (on the opposite side of the flange 45) coated with an adhesive material The sleeve lock 30 is mounted to its sleeve S by first "opening" the wall members 31 and 32 as shown in FIGS. 1 and 2 to admit the sleeve S between the inner surfaces of the two wall members 31 and 32. The two wall members 31 and 32 are then closed as shown by the arrows in FIGS. 1 and 2 so as to tightly hug the sleeve S therebetween. Thereafter, the tongue-like protrusion 42 of the hooking piece 38 is pressed downward (with reference to FIG. 1) such that the hooking piece 38 engages with the cross-sectionally U-shaped piece 37 to thereby keep the lock 30 in the locked condition.

It is to be noted that the position of the sleeve lock 30 can be easily adjusted with respect to the sleeve S. This can be done simply by lifting the tongue-like protrusion 42 to release the hooking piece 38 from the cross-sectionally U-shaped piece 37 and opening the wall members 31 and 32. After it is ascertained that the sleeve S has reached a body cavity of interest, the position of the sleeve lock 30 can thus be adjusted such that the pads 46 can effectively reach the patient's body. The pads 46 are then pressed against the patient's body surface around the opening. The pads 46 stick to the patient's body securely because of their surface coating of the adhesive material. Thus, the trocar sleeve S becomes securely anchored to the patient's body.

FIGS. 3 and 4 show another sleeve lock 50 embodying the present invention, characterized as having a generally U-shaped flat sleeve-holding member 51 for frictionally attaching to a tubular trocar sleeve S (shown in FIG. 3 at a position before it is attached to the member 51) by completely and intimately surrounding it. The sleeve-holding member 51 is made of a material such as silicone rubber that is both deformably resilient and capable of providing friction to the trocar sleeve. As shown in FIG. 3, the generally U-shaped member 51 has a portion 52 of its inwardly facing wall shaped in a substantially circular form with its diameter substantially equal to that of the trocar sleeve S. A gateway 53, which connects the circular wall portion 52 to the exterior of the U-shaped member 51, is normally open (that is, when the member 51 is in its natural condition without any external force exerted thereon to deform it). A deformable pad 55, generally in the form of a circle with an adhesive surface on one side and having a circular opening at the center and a radially extending fan-shaped portion removed therefrom, is formed on the back surface (as viewed in FIGS. 3 and 4) of the member 51, molded as a single unit therewith and made of the same material thereas. The central opening of the pad 55 conforms with the circular inner wall portion 52 of the member 51 and the fan-shaped missing portion of the pad 55 coincides with the normally open gateway 53 of the U-shaped member 51, as best seen in FIG. 3.

When the sleeve lock 50 is attached to the trocar sleeve S, the U-shaped member 51 is slightly deformed to enlarge the gateway 53 such that the trocar sleeve S can be admitted laterally into the circular inner wall portion 52 at the center. Because the member 51 is resilient and the diameters of the trocar sleeve S and the circular inner wall 52 are approximately the same, the trocar sleeve S fits tightly inside the central opening of the member 51 (not shown in the sleeve-holding condition). In order to keep the trocar sleeve S in this tightly fit condition such that the trocar sleeve S will not slide longitudinally through the member 51, there is provided a flexible tape 56 with a sticky surface. As shown by the arrow in FIG. 3, this sticky tape 56 is attached to the outer surface of the member 51 across its gateway 53. This, together with the friction-providing property of the circular inner surface 52 of the member 51, causes the sleeve lock 50 to be firmly attached to the trocar sleeve S.

It is to be noted that the position of this sleeve lock 50 can also be easily adjusted with respect to the sleeve S. This can be done simply by removing the adhesive tape 56 from one side of the gateway 53 as shown in FIG. 3 and deforming the member 51 to enlarge the gateway 53, or to weaken the compressive force of the inner wall 52 on the sleeve S enough to enable the sleeve lock 50 to slide longitudinally along the sleeve S. Thus, after it is ascertained that the sleeve S has reached a body cavity of interest, the position of the sleeve lock 30 is accordingly adjusted such that the pad 55 can effectively reach the patient's body. The pad 55 is then pressed against the patient's body surface around the opening. It is also to be noted that the sleeve S can be repositioned without releasing the lock 50 even after the lock 50 is closed because it is friction that holds the sleeve S in position FIGS. 5 and 6 show still another sleeve lock 60 of a spring clip type embodying the present invention. This spring clip sleeve lock 60 is structured somewhat similarly to the sleeve lock 50 described above with reference to FIGS. 3 and 4 in that there is a generally U-shaped sleeve-holding member 61 of a deformably resilient material such as silicone rubber with a circular opening 62 at its center. Unlike the sleeve lock 50 shown in FIGS. 3 and 4, however, the sleeve-holding member 61 according to this embodiment of the invention has the gateway 63 to this circular opening 62 normally closed.

In order to forcibly open the gateway 63 such that a tubular trocar sleeve can be admitted into the opening 62 at the center, a generally U-shaped metal clip 66 (like a common binder clip of the type which makes use of the elastic property of its metal) is embedded in the deformably resilient body of the sleeve-holding member 61 so as to generally conform with the U-shape of the latter as shown in FIG. 5. Extended parts 67 of the clip 66 for applying a force thereto in order to open the clip 66 protrude outside the member 61 so as to be accessible to the user. In its natural condition (that is, when no external force is being applied to the clip 66), the generally U-shaped sleeve-holding member 61 has its gateway 63 closed as shown in FIG. 5. When this sleeve lock 60 is to be mounted to a trocar sleeve (indicated by letter S in FIG. 6), the user pushes the extended parts 67 of the clip 66 towards each other as done commonly in using an ordinary binder clip. This causes to open not only the clip 66 but also the member 61 in which the clip 66 is embedded. Thus, the gateway 63 is opened wide enough for the trocar sleeve S to laterally pass through and to reach the central opening 62 or at least to be inserted longitudinally thereinto. After the trocar sleeve S is inserted into the central opening 62, the force being applied to the extended parts 67 of the clip 66 is released, causing the clip 66 to snap back to its original natural shape as shown in FIG. 5 due to the elastic force of its metallic material. Because the member 61 is of a friction-providing material, the trocar sleeve S is prevented from sliding longitudinally through the central opening 62 of the sleeve lock 60.

A nearly circular deformable pad 65 with an adhesive back surface (as viewed in FIGS. 5 and 6) is molded integrally with the resilient member 61, the clip 66 being insert-molded into the pad 65 and the member 61. Alternatively, a pad having a circular opening at the center and a radial slit may be attached to the back surface (as viewed in FIGS. 5 and 6) of the member 61 such that the circular opening and the slit will conform respectively to the center opening 62 and the gateway 63 of the member 61.

The position of this sleeve lock 60 is similarly adjustable with respect to the sleeve S. This can be done simply by pressing the extended parts 64 of the clip 66 to slightly open the gateway 63, or to weaken the grip of the member 61 on the sleeve S enough to enable the sleeve S to slide longitudinally through the opening 62. After it is ascertained that the sleeve S has reached a body cavity of interest, the position of the sleeve lock 60 is accordingly adjusted such that the pad 65 can effectively reach the patient's body. The pad 65 is then pressed against the patient's body surface around the opening. Regarding this embodiment, too, it is to be noted that the clip 66 need not be pressed to allow the sleeve S to be repositioned because it is the friction with the resilient member 61 that holds the sleeve S.

The present invention has been described above by way of only a few examples, but these examples are intended to be illustrative and not limitative. Many modifications and variations are possible within the scope of the invention. For example, many different types of locking device such as a snap lock of a commonly known kind may be substituted for connecting the two wall members 31 and 32 in the embodiment shown in FIGS. 1 and 2 or for the flexible tape 56 shown in FIGS. 3 and 4.

FIG. 7 shows a washer sleeve lock 70 embodying the present invention, comprised of an annular rubber washer 71 with a circular opening and a pad 72 with an adhesive surface. The inner diameter of the washer 71 is such that a trocar sleeve S (shown by a broken line), for which it is intended, can longitudinally squeeze through the washer 71 but experiences enough friction therefrom so as not to easily slide therethrough. After the sleeve lock 70 is thus mounted to the sleeve S and the sleeve S is inserted into an opening made by its obturator (not shown), it is still possible to adjust the longitudinal position of the lock 70 with respect to the sleeve S by manually expanding the elastic rubber material of the washer 71. The pad 72 with an adhesive surface is then pasted onto the patient's body for anchoring the sleeve S.

As a variation of the above, the washer 71 may be sandwiched between two pads 72 and 72' as shown schematically by the arrows in FIG. 8. The adhesive on one pad 72 holds the washer 71 on the other pad 72', the adhesive on which serves to be pasted on the patient's body. As a further variation, use may be made of a flange-like one-piece elastomer member as shown at 75 in FIGS. 9 and 10 with a center portion made somewhat thicker to provide a sufficient frictional force on the sleeve S inserted through its central opening 76. In FIG. 9, numeral 77 indicates a tab which is molded integrally to and protrudes from the main body of the member 75. The protruding tab 77 has no adhesive backing and serves to allow easy removal of the member 75 from the patient's skin.

As another example, FIG. 11 shows another washer sleeve lock 80 embodying the present invention, comprised of an elastomer washer 81 with a generally circular opening with a wavy peripheral line and a pad 82 with an adhesive surface. The dimension of the generally circular opening of the washer 81 is such that a trocar sleeve S (shown by a broken line), for which it is intended, can squeeze through the washer 81 by flexing the wavy peripheral edge portion of the opening but experiences enough friction from such flexed portion so as not to easily slide therethrough. After the sleeve lock 80 is thus mounted to the sleeve S and the sleeve S is inserted into an opening made by the trocar, it is still possible to adjust the longitudinal position of the lock 80 with respect to the sleeve S and the pad 82 with an adhesive surface is pasted onto the patient's body for anchoring the sleeve S. As a variation of the above, the washer 81 may be sandwiched between two pads (not shown) of the type shown at 82 similarly to the embodiment described above with reference to FIG. 8.

As still another example, FIG. 12 shows a skin-clip type of sleeve lock 90 embodying the present invention, comprised of an elastomer washer 91 with a generally circular opening with a wavy peripheral line similar to the one shown in, and described above with reference to FIG. 11. The washer 91 is elongated in one direction and supports a normally-closed elastic clip 92 of a simple structure made of a single piece of wire and having sharp tips 93 at both ends. After the sleeve lock 90 is mounted to a trocar sleeve S (shown by a broken line), the trocar sleeve S is inserted into an opening made by the trocar (not shown) and the longitudinal position of the lock 90 is properly adjusted with respect to the sleeve S as described above with reference to FIG. 11. The clip 92 is manually operated to cause its tips to open and then close so as to penetrate the patient's skin and to thereby anchor the sleeve S to the patient's body.

FIG. 13 shows a snap-on type of sleeve lock 95 as a further embodiment of the present invention, comprised of a single piece of a flexible material with a pad-like portion 96 having an adhesive surface and an elongated tape-like portion 97 having a friction-providing pad 98 and a snap 99. The tape-like portion 97 is dimensioned according to the size of the tubular trocar sleeve S around which it is intended to be wrapped such that, when it is snapped, the friction-providing pad 98 applies sufficiently strong pressure on the sleeve S so as to prevent it from easily sliding off against its frictional force. After the sleeve S is properly positioned and the position of the lock 95 with respect to the sleeve S is properly adjusted, the snap 99 is closed and the pad 96 with an adhesive surface is pressed against the patient's body to anchor the sleeve S to the patient's body as in previous examples.

Instead of a pad with an adhesive surface for attachment to the patient's body, use may alternatively be made of so-called skin staples to fasten the pad to the patient's body. FIG. 14 shows still another sleeve lock 100 comprised of a rubber washer 101 of the type shown at 71 in FIG. 7 and a crossbar 102 connected by an anchoring cord 103. One or two skin staples are placed over the cord 103 and the crossbar 102 serves to prevent the cord 103 from sliding away from the anchored position.

In summary, it is to be understood that many modifications and variations that may be apparent to a person skilled in the art are intended to be included within the scope of this invention.

What is claimed is:

1. A device for anchoring to a patient's body an elongated tubular trocar sleeve inserted into an opening formed in said patient's body, said device comprising sleeve-holding means for securely attaching to said trocar sleeve and skin-fixation means for attaching said device to said patient's body, said sleeve-holding and skin-fixation means being attached to each other, said sleeve-holding means allowing its position to be adjusted longitudinally along said sleeve and including an annular washer made of an elastic material, said skin-fixation means including a crossbar and a cord attached to said washer at one end and to said crossbar at the other, said cord being adapted to be stapled to said patient's body.

2. A device for anchoring to a patient's body an elongated tubular trocar sleeve inserted into an opening formed in said patient's body, said device comprising sleeve-holding means for securely attaching to said trocar sleeve and skin-fixation means for attaching said device to said patient's body, said sleeve-holding and skin-fixation means being formed integrally with respect to each other, said sleeve-holding means allowing its position to be adjusted longitudinally along said sleeve and including an annular washer made of an elastic material, said skin-fixation means including a crossbar and a cord attached to said washer at one end and to said crossbar at the other, said cord being adapted to be stapled to said patient's body.

* * * * *